United States Patent [19]
Revell

[11] Patent Number: 5,489,706
[45] Date of Patent: Feb. 6, 1996

US005489706A

[54] STABILIZED PERACID SOLUTIONS

[75] Inventor: Christopher Revell, Great Sankey, United Kingdom

[73] Assignee: Solvay Interox Limited, Warrington, United Kingdom

[21] Appl. No.: 244,026

[22] PCT Filed: Nov. 11, 1992

[86] PCT No.: PCT/GB92/02087

§ 371 Date: May 13, 1994

§ 102(e) Date: May 13, 1994

[87] PCT Pub. No.: WO93/10088

PCT Pub. Date: May 27, 1993

[30] Foreign Application Priority Data

Nov. 14, 1991 [GB] United Kingdom ............... 9124160

[51] Int. Cl.$^6$ ............................................. C07C 179/133

[52] U.S. Cl. ............................................. 562/3; 562/2

[58] Field of Search ............................................. 562/2, 3

[56] References Cited

U.S. PATENT DOCUMENTS 4,743,447 5/1988 Le Rouzic et al. ............... 424/130

FOREIGN PATENT DOCUMENTS 0193416 3/1986 European Pat. Off.

Primary Examiner—José G. Dees
Assistant Examiner—Samuel Barts
Attorney, Agent, or Firm—Larson and Taylor

[57] ABSTRACT

Disclosed is a process for improving the storage stability of peracetic acid comprising adding an effective concentration of preferably 0.1–5 wt. % of an aliphatic alcohol ethoxylate wetting agent which has an EO number of greater than 4.

19 Claims, No Drawings

STABILIZED PERACID SOLUTIONS

This application is a 371 of PCT/GB92/02087 filed Nov. 11, 1992.

The present invention relates to stabilised peracid solutions and their production.

Soluble peracids have a number of attractive properties, including oxidative and broad spectrum biocidal properties. As a consequence, they have been employed or proposed for use as oxidising agents in chemical synthesis reactions, as bleaching agents in the bleaching or cleansing of laundry and other substrates and as disinfectants or sterilisers for especially liquid media or solid surfaces.

One peracid which is widely available and suitable for the above-mentioned uses is peracetic acid which is usually produced in an aqueous solution by reaction between acetic acid and hydrogen peroxide, optionally in the presence of a catalyst such as a strong acid, including sulphuric, phosphoric and/or phosphonic acids. In a number of commercially available peracetic acid-containing compositions, the peracetic acid is present in equilibrium with the two reactants from which it is produced and water. Although such compositions may be used immediately after their production, they are often stored for considerable periods during their distribution and/or by the end user. During storage there is a tendency for some decomposition of the peroxygen species to occur, thereby progressively impairing the effectiveness of the composition for its desired purpose or requiring the use of an increased amount to attain a desired concentration of active ingredient. Plainly, therefore, it is desirable to find ways of improving the stability of peracid compositions, by which is meant ways of ameliorating or inhibiting the rate at which the measured concentration of peroxygen compounds and particularly peracetic acid falls during storage. One method of apparently improving the peracid stability in peracid compositions is described by Henkel in British Patent Specification no 1 580 561, which comprises employing a higher concentration of hydrogen peroxide relative to the peracetic acid than an equilibrium concentration. Essentially the same concept is disclosed in European Patent 0 024 125 to L'Air Liquide, but augmented by simultaneously diluting the acid catalyst below a minimal level so as to retard the rate of re-equilibration of the composition. By using excess hydrogen peroxide inventors seek to balance peracetic acid generation arising from slow re-equilibration against its rate of decomposition. Disadvantageously, the use of a considerable excess of one of the reagents inevitably increases the cost of the final product.

An alternative method of improving the storage stability of peracetic acid solutions has been proposed in European Patent 0 147 207 to Albright & Wilson, namely the incorporation of certain C6–C18 alkyl substituted benzene sulphonate wetting agents. In the course of the present investigations, it has been found that certain other wetting agents can be even more effective than alkyl benzene sulphonates at stabilising peracetic acid solutions.

According to one aspect of the present invention, there is provided a process for improving the storage stability of peracetic acid in a solution containing a wetting agent characterised by introducing therein an effective concentration of an aliphatic alcohol ethoxylate wetting agent which has an EO number of greater than 4.

According to a second aspect of the invention, there are provided peracetic acid solutions having improved storage stability by introduction therein of an effective concentration of an aliphatic alcohol ethoxylate wetting agent which has an EO number of greater than 4.

Advantageously, it has been found that the introduction of the specified wetting agent improves the retention of the important constituent, namely the peracetic acid in solution relative to like compositions containing no wetting agent or an alkyl benzene sulphonate, though it may not improve the retention overall of peroxygen species in the solution during storage. In general, peracetic acid solutions are stored at ambient temperature, which can vary depending upon the locality and the time of year, but is often between about 0° and 35° C.

The amount of aliphatic alcohol ethoxylate employed in the processes and compositions of the present invention preferably is at least 0.1%, particularly at least 0.2% w/w and often at least 0.5% w/w of the peracetic acid solution. In many instances, its concentration in the solution is not greater than 5% w/w. In some embodiments a convenient range of concentrations combining the benefits of wetting and improved stability comprises from about 0.5 to about 2.5% w/w of the solution.

The aliphatic alcohol ethoxylates employed herein preferably have an EO number of at least 6, often up to about 25, and usually, on average, between about 8 and about 20. It will be recognised though that the EO number is an average and in individual molecules, the number of ethylene oxide units can be below, within or above the ranges stated above. The alcohol moiety preferably contains at least 6 carbons and often up to about 20 carbons on average. In many alcohol ethoxylates that are suitable for the present invention, the alcohol moiety contains on average a chain length of from 8 to 18 carbons. The alcohol moiety is often either a primary or a secondary alcohol. The alcohol ethoxylate can be introduced into the peracetic acid solution either during its manufacture or when it has been produced. Thus, in one variation, the alcohol ethoxylate is mixed with the reactants which form peracetic acid, viz the acetic acid and aqueous hydrogen peroxide solution, and the mixture is stored until a desired proportion of the reactants have been converted to peracetic acid. Conventional variants in the manufacturing process can be employed. Thus, optionally, the manufacture can employ a strong acid catalyst selected at the operator's discretion, often in the range of from 0.1 to 10% w/w and selected from sulphuric acid, phosphoric acid and organic phosphonic acids (e.g. hydroxyethylenediphosphonic acid) or a mixture of mineral acid and organic phosphonic acid. A suitable reaction temperature can be selected at the operator's discretion at from 5° to 95° C., and often from 15° to 60° C. Suitable reaction times, which can vary from minutes to days depending upon the reaction temperature and amount of catalyst present, can be calculated from published data, for example broadly as set out in a paper by Y. Sawaki and Y. Ogata published in December 1965 in the Bulletin of the Chemical Society of Japan vol 38 no 12, pp2103/6. Naturally, conventional and appropriate safety precautions are taken during manufacture that are commensurate with the selected reaction conditions, such as the use of an inert atmosphere-at elevated reaction temperatures and adequate agitation of the mixture.

The concentration of peracetic acid in solution can be selected within a wide range, depending on its intended end use. Its concentration is usually at least 0.01% w/w often at least 0.1% w/w and normally up to about 40% w/w. In many instances, the peracetic acid concentration is from about 0.03% to about 15%; ready to use mixtures conveniently containing from 0.03 to 5% and dilutable concentrates often containing from about 10 to 15% w/w. The amounts of reactants can be selected to leave residual concentrations of them, viz hydrogen peroxide and acetic acid within wide ranges, typically each having a selected residual in the range of from about 1 to about 40% w/w. The amounts of reagents to use can be calculated using data on the equilibrium point of the reaction. For many ready to use mixtures, the reactants concentrations are each often chosen in the range of up to about 15% w/w and for dilutable concentrates they are often chosen in the range of about 10 to about 30% w/w. It will be understood, of course, that where the compositions, as made, differ to a significant extent from the corresponding equilibrium mixture, there will be a tendency for further or re-equilibration to occur during subsequent storage.

The present invention is particularly applicable to peracetic acid compositions in which the peracetic acid, acetic acid, hydrogen peroxide and water therein are approximately in equilibrium.

For some purposes it is desirable to produce a peracetic acid solution which contains a wetting agent, but which also generates relatively little foaming on application. Advantageously, it has been found that the selection of alcohol ethoxylate according to the present invention can not only improve peracetic acid storage stability, but also enable a low-foaming wetting agent-containing composition to be formed.

The stabilised compositions of the present invention are especially suitable for spraying onto or otherwise contacting solid surfaces, for example equipment, apparatus, containers, pipework, work surfaces, sanitary ware and the like for the purposes of disinfecting or sanitising them, the wetting agent promoting contact between the solution and the surface.

Having described the invention in general terms, specific embodiments thereof will hereafter be described more explicitly, by way of example only.

Comparison 1 and 2 and Example 3

In each of these Comparisons and Example, a commercial equilibrated peracetic acid-containing composition was employed available from Interox Chemicals Ltd. under their trade mark PROXITANE 0510, and containing nominally 5% w/w peracetic acid, 10% w/w acetic acid and 20% w/w hydrogen peroxide. In Comparison 2 and Example 3, 1.2 parts by weight of wetting agent were mixed into the peracetic acid composition at laboratory ambient temperature, about 22° C. The mixtures were stored at laboratory ambient temperature in translucent polyethylene storage bottles. The peracetic acid and total available oxygen (Avox) contents of each composition were determined at intervals during the storage, and the values obtained after 58 weeks storage are compared with their respective initial values and expressed below as a percentage of PAA and Avox retained, rounded to the nearest whole number. The total Avox content was measured using a standard ferric iron catalysed thiosulphate/iodine titration, and the peracetic acid content was measured by subtracting from the total Avox content the hydrogen peroxide content obtained by ferroin-indicated titration with ceric sulphate solution.

TABLE 1

| | Wetting agent | % Retained | |
|---|---|---|---|
| | | PAA | Avox |
| Comparison 1 | No wetting agent | 86 | 90 |
| Comparison 2 | Alkylbenzenesulphonic acid (Alkyl = C12 approx) | 85 | 95 |
| Example 3 | alcohol ethoxylate (Alkyl = C9, EO = 8) | 88 | 91 |

From Table 1, it can be seen that the effect of employing the alkyl benzene sulphonic acid is to increase the overall Avox retention of the composition relative to the corresponding composition which did not contain wetting agent, but that the stability of the most active constituent, namely PAA, was actually slightly worse. On the other hand, when the alcohol ethoxylate was employed, the overall effect was to not only increase the stability slightly of the compositions when expressed as total Avox, but more importantly,. a significant contribution to this improvement arose from the rather greater increase in stability of the most active constituent, PAA. This demonstrates the superiority of the alcohol ethoxylate for PAA stabilisation compared with an alkylbenzenesulphonic acid.

The compositions produced and tested in the foregoing Comparisons and Example were also tested to show their foaming and wetting properties.

The wetting trial was conducted by observing how long it took for a standard drop of sample to be absorbed by a piece of cotton (Brunchweiller).

The foaming trial was conducted by allowing the whole of a sample of 25 mls of composition to flow under gravity from a height of 25 cms from a wide-tipped burette into a measuring cylinder (100 mls) of diameter 28 mms placed underneath. The volume of foam generated initially and still present after 5 minutes is given in Table 2 below.

TABLE 2

| | Wetting time (secs) | Volume of foam (mls) | |
|---|---|---|---|
| | | Initially | 5 minutes |
| Comparison 1 | >300 | 0 | 0 |
| Comparison 2 | 5 | 38 | 36 |
| Example 3 | 5 | 32 | 17 |

From Table 2, it can be seen that one effect of incorporating the wetting agent is that the ability of the composition to wet a surface is markedly improved, and that when the alcohol ethoxylate is employed the extent of foam generated is detectably less than if an alkylbenzenesulphonic acid is employed, and the foam breaks down more quickly.

Comparisons 4 and 5 and Examples 6 to 8

In each of these Comparisons and Examples a solution was employed comprising peracetic acid, acetic acid and 6% hydrogen peroxide. In Comparison 5 and Examples 6 to 8, 2% of commercially available alcohol ethoxylates specified in Table 3 are mixed in at ambient temperature, about 22° C., and stored in polyethylene sample bottles.

The peracetic acid, hydrogen peroxide and total Avox contents of the compositions were measured at the start of the storage period and at regular intervals thereafter. The results after 8 months storage are also included in Table 3.

TABLE 3

|  | Wetting Agent | | % Retained | |
| --- | --- | --- | --- | --- |
|  | EO number | Alkyl chain | PAA | Avox |
| Comparison 4 | No wetting agents | | 82 | 100 |
| Comparison 5 | 4 | C12 | 80 | 100 |
| Example 6 | 6.5 | C9 | 85 | 100 |
| Example 7 | 8 | C9-11 | 89 | 100 |
| Example 8 | 11 | C13/15 | 92 | 100 |

From Table 3, it can be seen that although the total Avox retention was the same for all the compositions tested, there was a very significant change in the proportion of peracetic acid retained. When the EO number was only 4, as in comparison 5, the proportion retained was no better than when no wetting agent was present, but as the EO number increased, the proportion of peracetic acid which was retained increased.

Comparisons 9 and 10 and Examples 11 to 14

In these Comparisons and Examples non-equilibrium solutions containing approximately 300 ppm peracetic acid were obtained by diluting the commercially available were obtained by diluting the commercially available peracetic acid composition of Comparison 1, PROXITANE 0510, with demineralised water. In comparison 10 and Examples 13 and 14, the composition was doped with 0.5% w/w sulphuric acid as re-equilibrium catalyst, and in Examples 11 to 14, the composition was mixed with a commercially available alcohol ethoxylate having an EO number of 7 and a 67%/33% mixture of C13 and C15 carbon chain lengths in the alcohol moiety. The compositions were stored in polyethylene bottles at ambient temperature, about 22° C., and the peracetic acid content measured periodically by a direct method thiosulphate/iodine titration at below −10° C. in ethane-1,2-diol. The results after 29 hours are listed in Table 4.

TABLE 4

|  | % Wetting Agent | % $H_2SO_4$ | % PAA |
| --- | --- | --- | --- |
| Comparison 9 | None |  | 70 |
| Comparison 10 | None | 0.5 | 56 |
| Example 11 | 0.2 | None | 80 |
| Example 12 | 1.0 | None | 100 |
| Example 13 | 0.2 | 0.5 | 60 |
| Example 14 | 1.0 | 0.5 | 100 |

From Table 4, it can be seen that the presence of the alcohol ethoxylate increased the proportion of peracetic acid retained in the composition, and that the effect was greater at the higher concentration of the wetting agent. This shows that the useful life of diluted non-equilibrium peracetic acid compositions can be extended by incorporating the selected alcohol ethoxylates according to the present invention.

I claim:

1. A process for improving the storage stability of peracetic acid solution, said process comprising introducing into said solution an aliphatic alcohol ethoxylate wetting agent which as an EO number of greater than 4 in an amount of a least 0.1% by weight and sufficient to improve the storage stability of the peracetic acid in the solution.

2. A process according to claim 1, wherein from 0.1 to 5% w/w of aliphatic alcohol ethoxylate is employed.

3. A process according to claim 2, wherein from 0.5 to 2.5% w/w of aliphatic alcohol ethoxylate is employed.

4. A process according to claim 1, wherein the aliphatic alcohol ethoxylate has an EO number of at least 6.

5. A process according to claim 4, wherein the aliphatic alcohol ethoxylate has an EO number of from 8 to about 20.

6. A process according to claim 1, wherein the alcohol moiety in the aliphatic alcohol ethoxylate contains at least 6 carbons.

7. A process according to claim 6, wherein the alcohol moiety in the aliphatic alcohol ethoxylate contains from 8 to 18 carbons.

8. A process according to claim 1, wherein the aliphatic alcohol ethoxylate is introduced into the mixture of reactants during the manufacture of the peracetic acid solution.

9. A process for improving the storage stability of peracetic acid solution, said process comprising introducing into said solution, from 0.5 to 2.5% w/w of an aliphatic alcohol ethoxylate wetting agent which has an EO number of from 8 to 20.

10. A process according to claim 1 or claim 9, wherein the solution to be stabilised contains from about 0.03 to about 15% w/w peracetic acid.

11. A peracetic acid solution having improved storage stability comprising an aliphatic alcohol ethoxylate wetting agent which has an EO number of greater than 4 in an amount of at least 0.1% by weight sufficient to improve the storage stability of the peracetic acid in the solution.

12. A solution according to claim 11, containing from 0.1 to 5% w/w of aliphatic alcohol ethoxylate.

13. A solution according to claim 12, containing from 0.5 to 2.5% w/w of aliphatic alcohol ethoxylate.

14. A solution according to claim 11, wherein the aliphatic alcohol ethoxylate has an EO number of at least 6.

15. A solution according to claim 14, wherein the aliphatic alcohol ethoxylate has an EO number of from about 8 to about 20.

16. A solution according to claim 11, wherein the alcohol moiety in the aliphatic alcohol ethoxylate contains at least 6 carbons.

17. A solution according to claim 16, wherein the alcohol moiety in the aliphatic alcohol ethoxylate contains from 8 to 18 carbons.

18. A peracetic acid solution having improved storage stability comprising from 0.5 to 2.5% w/w of an aliphatic alcohol ethoxylate wetting agent which has an EO number of from 8 to 20.

19. A solution according to claim 11 or 18, wherein the solution to be stabilised contains from about 0.03 to about 15% w/w peracetic acid.

* * * * *